United States Patent [19]

Kruper, Jr. et al.

[11] Patent Number: 4,663,467
[45] Date of Patent: May 5, 1987

[54] NOVEL PORPHYRINATE AND AMINE COMPOSITION USEFUL AS CATALYSTS IN THE PREPARATION OF ALKYLENE CARBONATES

[75] Inventors: William J. Kruper, Jr., Midland; David V. Dellar, Sanford, both of Mich.

[73] Assignee: The Dow Chemical Company, Midland, Mich.

[21] Appl. No.: 585,965

[22] Filed: Mar. 5, 1984

[51] Int. Cl.$^4$ .............................. C07D 317/36
[52] U.S. Cl. .................... 549/229; 549/230; 252/162
[58] Field of Search ................. 549/229, 230

[56] References Cited

U.S. PATENT DOCUMENTS 2,994,705  8/1961  Crosby et al. ............. 549/230
3,535,341 10/1970  Emmons et al. ............ 549/230
3,748,345  7/1973  De Pasquale ............... 549/229

OTHER PUBLICATIONS

Aida et al., *Makromol. Chem., Rapid Commun.*, 1, 677 (1980).
Aida et al., *Macromolecules*, 14, 1162 (1981).
Adler, *J. Org. Chem.*, 32, 476 (1967).
Aida et al., *J. Amer. Chem. Soc.*, 105, 1304 (1983).
Aida et al., *Macromolecules*, 15, 682 (1982).
Summerville et al., *J. Amer. Chem. Soc.*, 99(25), 8195 (1977).
Inoue et al., *Bull. Chem. Soc. Japan*, 50(4), 984 (1977).
Groves et al., *Inorg. Chem.*, 21(4), 1963 (1982).
Takeda et al., *Makromol. Chem.*, 179, 1377 (1978).

*Primary Examiner*—Christopher A. Henderson
*Attorney, Agent, or Firm*—Norman L. Sims; Christopher John Rudy

[57] ABSTRACT

This invention is a composition comprising
(a) a p-hydrocarbylphenylporphyrinato chromium or aluminum with axial counterions; and
(b) an aliphatic amine, a heterocyclic amine, an aromatic amine, a phosphine or a phosphine oxide.

Another aspect of this invention is a process for the preparation of an alkylene carbonate which comprises contacting an epoxide with a carbon dioxide in the presence of a catalytic amount of the hereinbefore-described composition.

18 Claims, 1 Drawing Figure

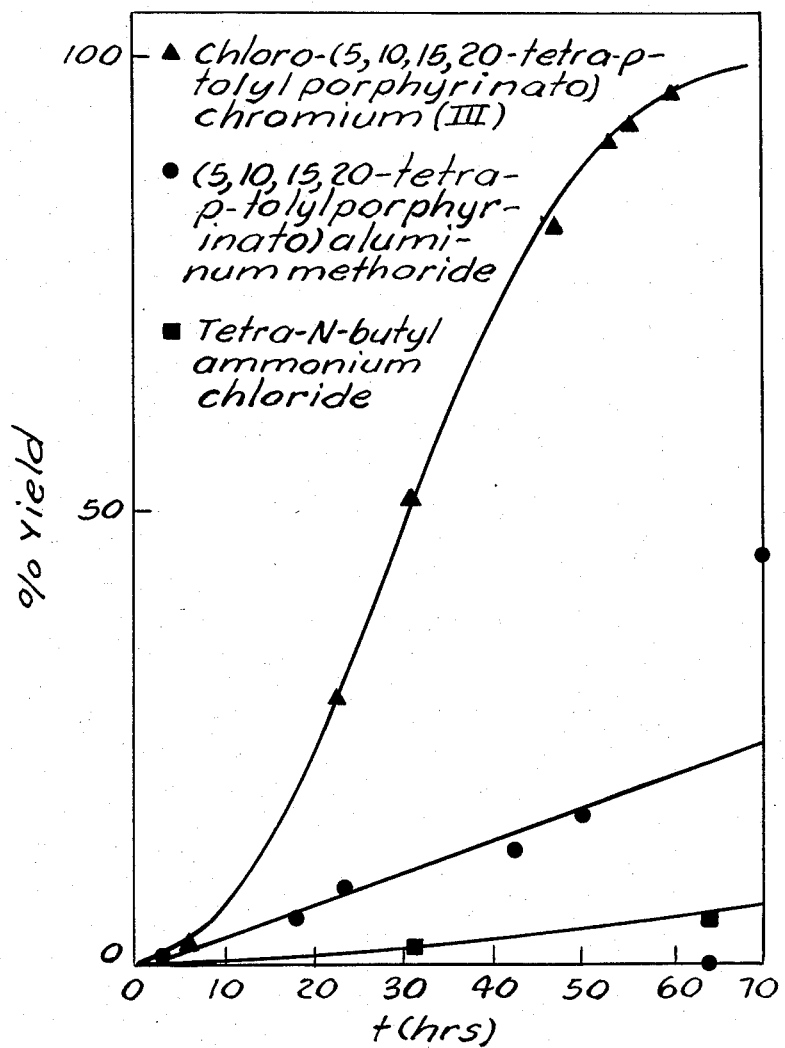

NOVEL PORPHYRINATE AND AMINE COMPOSITION USEFUL AS CATALYSTS IN THE PREPARATION OF ALKYLENE CARBONATES

BACKGROUND OF THE INVENTION

This invention relates to a novel porphyrinate and amine composition, which is useful as a catalyst in preparing alkylene carbonates.

Alkylene carbonates are useful in the preparation of polymers and glycols and as solvents.

The preparation of alkylene carbonates by reacting an alkylene oxide and carbon dioxide is well-known. The general conditions for the reaction are the use of temperatures in the approximate range of 100° C.–250° C. Superatmospheric pressures of about 10–300 atmospheres are employed. A reaction temperature of about 160° C.–200° C. and a pressure of 50–150 atmospheres are usually preferred. The reactants are used in about equal molar proportions with the carbon dioxide normally in slight excess.

Known catalysts for the reaction include inorganic bases such as sodium hydroxide and sodium carbonate and organic nitrogen bases such as tertiary amines, quaternary ammonium bases, and salts of these nitrogen bases such as their carbonates and halides. For example, aliphatic tertiary amines such as trimethylamine, aromatic tertiary amines such as pyridine and quinoline, quaternary ammonium hydroxides such as tetraethyl ammonium hydroxide, trimethylbenzyl ammonium hydroxide, dialkyl piperidinium hydroxide, and the carbonates, bicarbonates, and halides of such hydroxides are all known to catalyze the reaction. Catalyst concentrations of 0.1–5 percent based on the weight of alkylene oxide are conventional.

Other catalysts disclosed in the patent literature are anion-exchange resins containing quaternary ammonium chloride groups (U.S. Pat. No. 2,773,070), hydrazine or the hydrohalide salt thereof (U.S. Pat. No. 3,535,341) and guanidine and its salts (U.S. Pat. No. 3,535,342). Catalysts known to the art generally are effective for the purpose and they provide fairly high conversions of the reactants and generally good yields of the desired cyclic carbonates. These yields usually are about 70–90 percent of the theoretical. The latter two patents claim conversions and yields each in excess of 95 percent.

In commercial processes the ammonium halide and anion-exchange resins containing the ammonium halides are the most common catalysts.

There are several problems with the above-described processes. The alkylene carbonates prepared by such processes contain troublesome impurities. Some of these impurities result in a colored product. Further, it has been found that the anion-exchange resin catalysts tend to lose their catalytic activity over a period of use.

A process for the preparation of alkylene carbonates in which the catalyst has long lifetimes, can be recovered easily and repeatedly used, is desirable. Further, a catalyst which does not degrade to form undesirable impurities is needed.

SUMMARY OF THE INVENTION

This invention is a composition comprising
(a) a p-hydrocarbylphenyl porphyrinato chromium or aluminum with axial counterions; and
(b) an aliphatic amine, a heterocyclic amine, an aromatic amine, a phosphine or phosphine oxide.

Another aspect of this invention is a process for the preparation of alkylene carbonates (1,3-dioxalan-2-ones) which comprises contacting an epoxide and carbon dioxide in the presence of a catalytic amount of a catalyst which comprises
(a) a p-hydrocarbylphenol porphyrinato chromium or aluminum with an axial counterion; and
(b) an aliphatic amine, an aromatic amine, a phosphine or a phosphine oxide under conditions such that an alkylene carbonate is prepared.

The novel porphyrinate and amine composition of this invention has several advantages. First, as a catalyst in the production of alkylene carbonates, such catalysts have increased lifetimes. These catalysts can be easily recovered and recycled repeatedly. Furthermore, these catalysts do not degrade so as to prepare impurities which create problems in the products.

DESCRIPTION OF FIGURES

The FIGURE is a plot of the yield of butylene carbonate versus time wherein three different catalysts are used, in particular, chloro-(5,10,15,20-tetra-p-tolylporphyrinato)chromium (III); (5,10,15,20-tetra-p-tolylporphyrinato)aluminum methoxide; and tetra-N-butyl ammonium chloride. The experiment is further described in Example 13.

DETAILED DESCRIPTION OF THE INVENTION

Included among porphyrinates useful in this invention are p-hydrocarbylphenyl porphyrinato chromium or aluminum (hereinafter porphyrinates) wherein the aluminum is in the +3 oxidation state and the chromium is in the +2, +3 or +4 oxidation state. Porphyrinates wherein the aluminum or chromium is in the +3 oxidation state are preferred. The porphyrinates useful in this invention have axial counterions bonded to the chromium or aluminum and such axial counterions are generally anions.

Porphyrinates useful in this invention include those which correspond to the formula

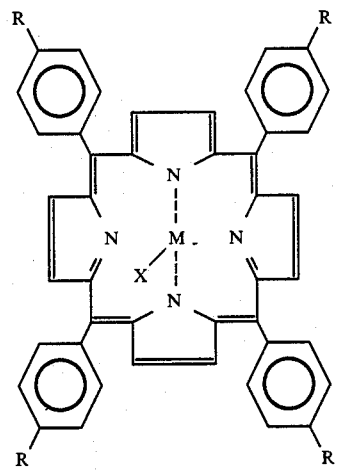

wherein M is chromium or aluminum; R is a hydrocarbyl moiety; and X is a halide, alkoxide, azide, cyanide, isocyanide, perchlorate, fluoroborate, nitride or oxo moiety.

In the above formula, M is preferably chromium. R is preferably a $C_{1-20}$ alkyl, $C_{6-20}$ aryl, $C_{7-20}$ alkaryl or $C_{7-20}$ aralkyl moiety. R is more preferably a $C_{1-20}$ alkyl moiety, with a $C_{1-10}$ alkyl moiety being even more preferred. R is most preferably a $C_{1-4}$ alkyl moiety. X is more preferably a halide, alkoxide, azide, cyanide, oxo or isocyanide moiety; most preferably a halide.

Examples of porphyrinates within the scope of this invention include chloro-(5,10,15,20-tetra-p-tolylporphyrinato)chromium (III); oxo-(5,10,15,20-tetra-p-tolylporphyrinato)chromium (IV); bromo-(5,10,15,20-tetra-p-tolylporphyrinato)chromium (III); chloro-(5,10,15,20-tetra-p-ethylphenylporphyrinato)chromium (III); oxo-(5,10,15,20-tetra-p-ethylphenylporphyrinato)chromium (IV); bromo-(5,10,15,20-tetra-p-ethylphenylporphyrinato)chromium (III); (5,10,15,20-tetratolylporphyrinato)chromium (III) methoxide; (5,10,15,20-tetratolylporphyrinato)aluminum (III) methoxide, and (5,10,15,20-tetraphenylporphyrinato)aluminum (III) ethoxide.

Co-catalysts in this invention include amines, phosphines and phosphine oxides. Amines useful in this invention include aliphatic amines, heterocyclic amines and aromatic amines. Examples of amines which can be used in this invention include the following: monoalkylamines including methylamine, ethylamine, propylamine, isopropylamine, n-butylamine, sec-butylamine, isobutylamine, pentylamines, hexylamines, cyclohexylamines, heptylamines, octylamines, dodecylamines, octadecylamines, eicosylamines, triacontanylamines, benzylamine, chlorobenzylamine, nitrobenzylamine, 2-ethoxyethylamine, 4-carbomethoxyhexylamine, etc.; dialkylamines including dimethylamine, diethylamine, di-n-propylamine, diisopropylamine, di-n-butylamine, di-sec-butylamine, diisobutylamine, di-tert-butylamine, dipentylamines, dihexylamines, dioctylamines, ditriacontanylamine, N-methylethylamine, N-methylpropylamine, N-methyloctadecylamine, N-ethylhexylamine, N-ethyldodecylamine, N-propyldodecylamine, etc.; heterocyclic aliphatic secondary amines including piperidine, pyrrole, imidazoline, pyrazole, piperazine, etc.; arylamines including aniline, toluidine, anisidine, nitroaniline, bromoaniline, xylidines, 4-ethylaniline, naphthylamine, etc; diarylamines including diphenylamine, N-phenyl-2-nephthylamine, N-phenylnaphthylamine, etc.; alkyl arylamine having from 1 to about 30 carbon atoms in the alkyl group attached either to the nitrogen atom or to the aryl group including N-ethylaniline, N-methyl-o-toluidine, N-methyl-p-toluidine, p-chloro-N-methylaniline, N,N'-dimethylphenylenediamine, 4-ethylaniline, 4-propylaniline, 4-butylaniline, 4-decylaniline, etc.; and aminoalkyl-substituted amines including ethylenediamine, diethylenetriamine, triethylenetetramine, 1,3-propylenediamine, di-1,3-propylenetriamine, 1,6-11,16-tetraazahexadecane.

Preferred amines are the heterocyclic and aromatic amines. Among examples of preferred amines are 4-dimethylaminopyridine, 4-cyanopyridine, 4-chloropyridine, 1-methylimidazole and 2-methylimidazole.

Phosphines comprise a phosphorus atom substituted with three ligands and those useful in this process correspond to the formula $P(Y)_3$ wherein Y is separately in each occurrence a $C_{1-20}$ hydrocarbyl moiety, preferably alkyl or aryl. Examples of phosphines include triphenylphosphine, trimethylphosphine, triethylphosphine and tripropylphosphine.

Phosphine oxides comprise a phosphorus atom which is doubly bonded to an oxygen and wherein the phosphorus atom is further substituted with 3 ligands, and those useful in this process correspond to the formula

wherein Y is as defined hereinbefore.

The preferred co-catalysts are the amines and phosphines, with the amines being the most preferred co-catalyst species.

The preferred co-catalyst to porphyrinate ratio is between about 1:1 and 20:1, more preferably between about 4:1 and 10:1, with between about 4:1 and 6:1 being most preferred.

The porphyrinates useful in this invention are known compounds and may be prepared by the techniques described in Adler, *J. Org. Chem.*, 32, 476 (1967); Inoue et al., *Bull. Chem. Soc. Jap.*, 50 (4), 984 (1977); Takeda, *Makromolecular Chem.*, 179, 1377 (1978); Groves et al., *Inorg. Chem.*, 21, 1363 (1982); Aida et al., *Macromolecules*, 14, 1162 (1981); Aida et al., *Macromolecular Chemistry, Rapid Communications*, 1, 677 (1980); and Summerville et al., *J. Amer. Chem. Soc.*, 99 (25), 8195 (1977) (all incorporated herein by reference).

Tetra-p-hydrocarbylphenylporphyrines are prepared by contacting pyrrolidine and p-hydrocarbyl-substituted benzaldehydes in refluxing propionic acid, for about 30 minuntes. After reflux, the solution is cooled to room temperature and filtered, and the filter cake washed thoroughly with methanol. After a hot water wash, the resulting crystals are air dried, and finally dried in vacuo to remove any absorbed acid.

Chloro-(5,10,15,20-p-hydrocarbylphenylporphyrinato)chromium (III) is prepared by dissolving tetra-p-hydrocarbylphenylporphyrines in refluxing dimethylformamide and thereafter contacting with the solution chromium dichloride and refluxing until no more of the tetra-p-hydrocarbylphenylporphyrinate is present. The reaction mixture is thereafter cooled and poured into a reaction flask containing water at about 0° C. The resulting precipitate is collected by filtration and washed with water and dried in a vacuum for about 1 hour at about 100° C.

The chloro-(5,10,15,20-tetra-p-hydrocarbylphenylporphyrinato)chromium (III) can be converted to the oxo-(5,10,15,20-tetra-p-hydrocarbylphenylporphyrinato)chromium (IV) by reacting chloro-(5,10,15,20-tetra-p-hycrocarbylphenylporphyrinato)chromium (III) with iodosylbenzene and base, for example, tert-butyl-hydroperoxide, m-chloroperoxybenzoic acid, or sodium hypochlorite to produce the oxo chromium species. The porphyrinates with chlorine as the axial counterion can be converted to porphyrinates with other axial counterions by a ligand-exchange. This is done by dissolving the porphyrinate with the chlorine axial counterion in an aqueous solution and contacting the aqueous solution with an alkali metal salt which contains the counterion to be ligand-exchanged with the chlorine in the presence of a phase-transfer catalyst at room temperature.

The aluminum porphyrinates are prepared by reacting tetra-p-hydrocarbylphenyl porphyrines with a dialkyl ammonium halide in a dichloromethane solvent, in the absence of oxygen. The chloride counterion can be ligand-exchanged as described hereinbefore.

The novel composition of this invention is useful as a catalyst for the preparation of alkylene carbonates from epoxides and carbon dioxide.

Desirable epoxides include those corresponding to the formula

wherein
$R^1$ is separately in each occurrence hydrogen, halogen, a nitro group, a cyano group or a monovalent hydrocarbon $C_{1-20}$ or a monovalent hydrocarbon $C_{1-20}$ substituted with one or more of the following: a halo, cyano, nitro, thioalkyl, tert-amino, alkoxy, aryloxy, aralkoxy, carbonyldioxyalkyl, carbonyldioxyaryl, carbonyldioxyaralkyl, alkoxycarbonyl, aryloxycarbonyl, aralkoxycarbonyl, alkylcarbonyl, arylcarbonyl, aralkylcarbonyl, alkylsulfinyl, arylsulfinyl, aralkylsulfinyl, alkylsulfonyl, arylsulfonyl or aralkylsulfonyl group, or two $R^1$'s either on the same carbon atom or adjacent carbon atoms may combine to form a cycloaliphatic group.

$R^1$ is preferably hydrogen, a monovalent $C_{1-20}$ alkane, $C_{1-20}$ haloalkane, a $C_{1-20}$ alkene, a $C_{1-20}$ alkane further substituted by an alkoxy, aryloxy, alkaryloxy or aralkyloxy moiety, or two $R^1$'s, either on the same or adjacent carbon atoms, may combine to form a cycloaliphatic group. $R^1$ is most preferably hydrogen or methyl.

Among desirable epoxides are the alkylene oxides, for instance ethylene oxide, propylene oxide, butylene oxide; epihalohydrins, such as epibromohydrin and epichlorohydrin; styrene oxide, vinylene oxide, cyclohexene oxide, cyclopentene oxide, cycloheptane oxide, 2,3-epoxy propylphenyl ether and tert-butyl glycidyl ether. Among preferred epoxides are ethylene oxide, propylene oxide, epichlorohydrin, epibromohydrin, styrene oxide and vinylene oxide. Among more preferred epoxides are propylene oxide and butylene oxide.

Alkylene carbonates prepared by the process of this invention include those corresponding to the formula

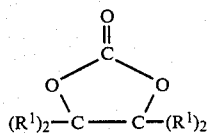

wherein $R^1$ is as defined above.

Examples of desirable alkylene carbonates include ethylene carbonate, propylene carbonate, butylene carbonate, vinylene carbonate and phenylene carbonate. More preferred alkylene carbonates include butylene carbonate and propylene carbonate.

$C_{1-20}$ hydrocarbyl means herein an organic radical containing between one and twenty carbon atoms to which are bonded hydrogen atoms. Included are the following groups: $C_{1-20}$ alkyl, $C_{1-20}$ alkenyl, $C_{1-20}$ alkynyl, $C_{3-20}$ cycloalkyl, $C_{3-20}$ cycloalkenyl, $C_{6-20}$ aryl, $C_{7-20}$ alkaryl or $C_{7-20}$ aralkyl.

The term aryl refers herein to biaryl, phenyl, naphthyl, phenanthranyl and anthranyl. Alkaryl refers herein to an alkyl-, alkenyl- or alkynyl-substituted aryl substituent wherein aryl is as defined hereinbefore. Aralkyl means herein an alkyl, alkenyl or alkynyl substituent substituted with an aryl group, wherein aryl is as defined hereinbefore.

$C_{3-20}$ cycloalkyl refers to an alkyl group containing one, two, three or more cyclic rings. $C_{3-20}$ cycloalkenyl refers to mono-, di- and polycyclic groups containing one or more double bonds. $C_{3-20}$ cycloalkenyl also refers to the cycloalkenyl groups wherein two or more double bonds are present.

In general the epoxide and carbon dioxide are reacted in any ratio which gives a suitable yield of the desired alkylene carbonate. Preferably the epoxide is contacted with an excess of carbon dioxide. In more preferable embodiments, the reaction is done under pressure wherein excess carbon dioxide is used to pressurize the reaction vessel. It is preferable to run the reaction at between about 100 and 1000 psia (689.47 and 6894.75 Pa) of pressure, with between about 600 and 800 psi (4136.85 and 5515.80 Pa) of pressure being more preferred.

The catalyst can be present in any amount which is catalytic for the reaction described hereinbefore. It is preferable to use an amount of catalyst which provides between about 0.005 and 10 mole percent of porphyrinate based upon the epoxide, preferably between about 0.01 and 1.0 mole percent, with between about 0.01 and 0.05 mole percent being most preferred.

The epoxide and carbon dioxide can either be contacted in neat form or in the presence of an inert organic solvent. It is preferable to run the reaction under neat conditions.

Suitable solvents include any inert organic solvent which dissolves the reactants. Organic solvents include aromatic hydrocarbons, aliphatic hydrocarbons, chlorinated aromatic hydrocarbons, aliphatic chlorinated hydrocarbons, cyclic ethers and aliphatic ethers. Examples of aromatic solvents include benzene, toluene, xylene, ethylbenzene and the like. Examples of aliphatic hydrocarbons include hexane, heptane, octane and the like. Examples of chlorinated aromatic hydrocarbons include monochlorobenzenes, dichlorobenzenes, trichlorobenzenes, monochlorotoluene, monochloroethylbenzene and the like. Chlorinated aliphatic hydrocarbons include chloromethane, dichloromethane, trichloromethane, tetrachloromethane, chloroethane, dichloroethane, 1,1,1-trichloroethane, vinyl chloride, vinylidene chloride and the like. Cyclic ethers include tetrahydrofuran and the like. Aliphatic ethers include ethyl ether and the like. Preferred solvents are chlorinated hydrocarbons.

This process can be run at any temperature at which the reaction proceeds. Preferable temperatures are between about 0° C. and 250° C. Between about 25° C. and 150° C. is more preferred, with between about 50° C. and 100° C. being most preferred. Below about 0° C. the reaction rate is extremely slow. Above 250° C. there is significant risk of thermal degradation of both products and reactants.

The porphyrinate catalysts can be recovered from the reaction mixture by distilling the product and solvent away. In order to remove any residual product from the porphyrinates, the porphyrinates can be dissolved in a solvent and thereafter eluted through a suitable adsorbent so as to separate the porphyrinates from the residual product. This can be done by a technique known as gravity chromatography using a column of silica gel or alumina.

The advantages of using the composition of this invention to catalyze the preparation of alkylene carbonates include the easy recovery of the porphyrinates; the porphyrinates can be used repeatedly; the porphyrinates do not degrade to prepare unwanted impurities; and the product can be easily distilled from the catalyst without leaving behind any impurities.

SPECIFIC EMBODIMENTS

The following examples are included for illustrative purposes and do not limit the scope of the claims or the invention. All parts and percentages are by weight unless otherwise specified.

EXPERIMENTAL PROCEDURE

An epoxide, porphyrinate catalyst and amine cocatalyst are added to a stainless steel autoclave equipped with a small magnetic stir bar. The autoclave is then sealed, pressurized with gaseous carbon dioxide with heating and stirring. After a specified reaction time the vessel is cautiously vented and the products distilled from the reaction mixture.

The following table demonstrates the conditions and results of Examples 1–12.

p-tetratolylporphyrinato)aluminum methoxide and 17 mg of dimethylaminopyridine along with 1-butylene oxide (11.5 g, 1.59 mmoles). The reactors are sealed and heated to 50° C. under a pressure of 780 psig of carbon dioxide with stirring. Samples are periodically taken and analyzed by vapor phase chromatography to determine the conversion rate. In a third reactor, tetra-N-butyl ammonium chloride (50 mg, 0.11 mole percent) is used as a catalyst under identical conditions. In the FIGURE a plot of the yield versus time of each of these three reactions is given. The FIGURE demonstrates that the porphyrinate catalysts exhibit a much faster reaction rate than the ammonium halides. The FIGURE further illustrates that the chromium porphyrinates demonstrate a much faster reaction rate than the aluminum porphyrinate. Further, the porphyrinates demonstrate a faster reaction rate than the ammonium salt catalyst.

What is claimed is:

1. A process for the preparation of alkylene carbonates which comprises contacting an epoxide and carbon dioxide in the presence of a catalytic amount of a catalyst which comprises
   (a) a p-hydrocarbylphenylporphyrinato chromium

TABLE I

| Example | Epoxide | Co-catalyst | Epoxide mass, g | Catalyst mass mg | Co-catalyst mass, mg | Temp °C. | Pressure psig | Time hr | Product | % Yield (distilled) |
|---|---|---|---|---|---|---|---|---|---|---|
| 1 | propylene oxide | N,N—dimethyl-aminopyridine | 16.3 | 25 | 25 | 80 | 720 | 84 | 4-methyl-1,3-dioxalan-2-one[1] | 95 |
| 2 | propylene oxide | N—methyl-imidazole | 16.4 | 25 | 25 | 80 | 750 | 48 | 4-methyl-1,3-dioxalan-2-one[1] | 99 |
| 3 | propylene oxide | N,N—dimethyl-aminopyridine | 20.5 | 25 | 25 | 60 | 780 | 40 | 4-methyl-1,3-dioxalan-2-one[1] | 100 |
| 4 | epichloro-hydrin | N,N—dimethyl-aminopyridine | | 25 | 25 | 60 | | 18 | 4-chloromethyl-1,3-dioxalan-2-one[2] | 99.8 |
| 5 | epichloro-hydrin | N—methyl-imidazole | 10.53 | 25 | 25 | 70 | 680 | 48 | 4-chloromethyl-1,3-dioxalan-2-one[2] | 100 |
| 6 | cyclohexene oxide | dimethyl-aminopyridine | 5.0 | 20 | 30 | 95 | 780 | 18 | 7,9-dioxabicyclo[4.3.0]nonan-8-one[3] | 97 |
| 7 | cyclohexene oxide | N—methyl-imidazole | 4.0 | 25 | 25 | 100 | 700 | 24 | 7,9-dioxabicyclo[4.3.0]nonan-8-one[3] | 85 |
| 8 | cyclopentene oxide | N—methyl-imidazole | 5.0 | 25 | 25 | 90 | 700 | 60 | 2,4-dioxabicyclo[3.3.0]octan-3-one[4] | 90 |
| 9 | cycloheptene oxide | N—methyl-imidazole | 2.0 | 12 | 12 | 85 | 700 | 22 | 8,10-dioxabicyclo[5.3.0]decan-9-one[5] | 97 |
| 10 | cycloheptene oxide | N—methyl-imidazole | | | | 85 | | 22 | 8,10-dioxabicyclo[5.3.0]decan-9-one[5] | 100 |
| 11 | 2,3-epoxy-propyl phenyl ether | N—methyl-imidazole | 10 | 25 | 25 | 70 | 780 | 16 | 4-phenoxymethyl-1,3-dioxalan-2-one | 100 |
| 12 | 1-butylene oxide | N,N—dimethyl-aminopyridine | 2 | 12 | 12 | 100 | 780 | 20 | 4,5-dimethyl-1,3-dioxalan-2-one[6] | 84 |

[1]Propylene carbonate
[2]Epichlorohydrin carbonate
[3]Cyclohexane carbonate
[4]Cyclopentene carbonate
[5]Cycloheptene carbonate
[6]Butylene oxide The catalyst in Examples 1 and 3–12 is chloro-(5,10,15,20-tetra-p-tolylporphyrinato)chromium (III). The catalyst in Example 2 is oxo-5,10,15,20-tetra-p-phenylporphyrinato)chromium (IV).

EXAMPLE 13

In separate reactors are placed chloro-(5,10,15,20-tetra-p-tolylporphyrinato)chromium (III) and (5,10,15,20- with an axial counter-ion wherein the chromium is in the +2, +3, or +4 oxidation state; and
   (b) a cocatalyst of an amine, a phosphine or a phosphine oxide under conditions such that an alkylene carbonate is prepared.

2. The process of claim 1 wherein the p-hydrocarbylphenylporphyrinato chromium corresponds to the formula

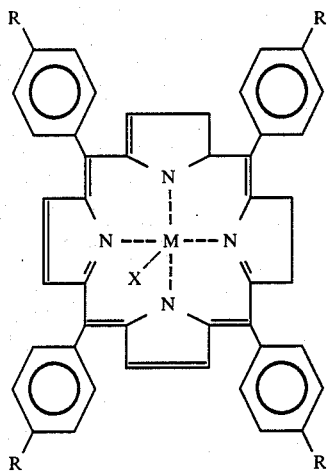

wherein
R is separately in each occurrence $C_{1-20}$ hydrocarbyl;
M is the chromium; and
X is a halide, alkoxide, azide, cyanide, isocyanide, perchlorate, fluoroborate, nitride or oxo moiety, and the phosphine corresponds to the formula $P(Y)_3$ wherein Y is separately in each occurrence a $C_{1-20}$ hydrocarbyl moiety, and the phosphine oxide corresponds to the formula

wherein Y is separately in each occurrence a $C_{1-20}$ hydrocarbyl moiety; and the cocatalyst and the p-hydrocarbylphenylporphyrinato chromium are present in an equivalent ratio of between about 1:1 and 20:1.

3. The process of claim 1 wherein the epoxide corresponds to the formula

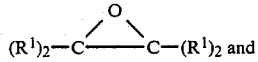

the alkylene carbonate corresponds to the formula

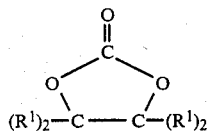

wherein
$R^1$ is separately in each occurrence hydrogen, halogen, a nitro group, a cyano group or a monovalent hydrocarbon $C_{1-20}$ or a monovalent hydrocarbon $C_{1-20}$ substituted with one or more of the following: a halo, cyano, nitro, thioalkyl, tert-amino, alkoxy, aryloxy, aralkoxy, carbonyldioxyalkyl, carbonyldioxyaryl, carbonyldioxyaralkyl, alkoxycarbonyl, aryloxycarbonyl, aralkoxycarbonyl, alkylcarbonyl, arylcarbonyl, aralkylcarbonyl, alkylsulfinyl, arylsulfinyl, aralkylsulfinyl, alkylsulfonyl, arylsulfonyl or aralkylsulfonyl group, or two $R^1$'s either on the same carbon atom or adjacent carbon atoms combined to form a cycloaliphatic group.

4. The process of claim 3 wherein
$R^1$ is separately in each occurrence hydrogen, a monovalent $C_{1-20}$ alkane, $C_{1-20}$ haloalkane, a $C_{1-20}$ alkene, a $C_{1-20}$ alkane further substituted by an alkoxy, aryloxy, alkaryloxy or aralkyloxy moiety, or two $R^1$'s, either on the same or adjacent carbon atoms, combined to form a cycloaliphatic group.

5. The process of claim 4 wherein $R^1$ is separately in each occurrence hydrogen or methyl.

6. The process of claim 2 wherein R is separately in each occurrence $C_{1-20}$ alkyl, $C_{6-20}$ aryl, $C_{7-20}$ alkaryl or $C_{7-20}$ aralkyl and M is $Cr^{+3}$, or $Cr^{+4}$.

7. The process of claim 2 wherein the epoxide is an alkylene oxide, an epihalohydrin, a vinylene oxide or a glycidyl ether.

8. The process of claim 7 wherein the epoxide is an alkylene oxide of ethylene oxide, propylene oxide, 1- or 2-butylene oxide, cyclopentene oxide, cyclohexene oxide, cycloheptene oxide or a styrene oxide; an epihalohydrin; or a glycidyl ether of 2,3-epoxy propylphenyl ether or tert-butyl glycidyl ether.

9. The process of claim 8 wherein the epoxide is the compound ethylene oxide, propylene oxide, 1- or 2-butylene oxide, cyclopentene oxide, cyclohexene oxide, cycloheptene oxide, epichlorohydrin, epibromohydrin, styrene oxide, 2,3-epoxy propylphenyl ether, or tert-butyl glycidyl ether.

10. The process of claim 9 wherein the epoxide is the compound propylene oxide, 1-butylene oxide, cyclopentene oxide, cyclohexene oxide, cycloheptene oxide, epichlorohydrin, or 2,3-epoxy propyl phenyl ether.

11. The process of claim 10 wherein the epoxide is the compound propylene oxide or 1-butylene oxide.

12. The process of claim 3 wherein the p-hydrocarbylphenylporphyrinato is (5,10,15,20-tetra-p-ethyl-, phenyl- or tolyl-porphyrinato)-chromium (III), chloride, bromide, methoxide or ethoxide; or (5,10,15,20-tetra-p-ethyl-, phenyl- or tolyl-porphyrinato)-chromium (IV) oxide and the cocatalyst is an amine.

13. The process of claim 6 wherein R is separately in each occurrence $C_{1-20}$ alkyl.

14. The process of claim 13 wherein the cocatalyst is an amine of an aliphatic amine, heterocyclic amine or aromatic amine and R is separately in each occurrence $C_{1-4}$ alkyl.

15. The process of claim 14 wherein the equivalent ratio of amine to porphyrinate is between about 4:1 and 10:1.

16. The process of claim 15 wherein a catalytic amount of the catalyst is between about 0.005 and 10 mole percent of the porphyrinate based upon the epoxide.

17. The process of claim 16 wherein the temperature is between 0° C. and 250° C.

18. The process of claim 17 wherein the pressure is between about 100 and 1000 psi.